United States Patent
Garlatti et al.

(10) Patent No.: US 12,396,762 B2
(45) Date of Patent: Aug. 26, 2025

(54) INTERSPINOUS VERTEBRAL DISTRACTOR

(71) Applicant: DIAMETROS MEDICAL S.R.L., Rome (IT)

(72) Inventors: Gianni Garlatti, San Casciano in Val di Pesa (IT); Lorenzo Fortuna, Pelago (IT)

(73) Assignee: DIAMETROS MEDICAL S.R.L., Rome (IT)

(*) Notice: Subject to any disclaimer, the term of this patent is extended or adjusted under 35 U.S.C. 154(b) by 175 days.

(21) Appl. No.: 17/938,183

(22) Filed: Oct. 5, 2022

(65) Prior Publication Data
US 2023/0027465 A1    Jan. 26, 2023

Related U.S. Application Data

(63) Continuation of application No. PCT/IB2020/053350, filed on Apr. 8, 2020, and a continuation of application No. PCT/IB2020/053352, filed on Apr. 8, 2020, and a continuation of application No. PCT/IB2020/053353, filed on Apr. 8, 2020.

(51) Int. Cl.
*A61B 17/70* (2006.01)

(52) U.S. Cl.
CPC ................ *A61B 17/7065* (2013.01)

(58) Field of Classification Search
CPC ...... A61B 17/7062–17/707; A61B 2017/0256; A61F 2/4405
See application file for complete search history.

(56) References Cited

U.S. PATENT DOCUMENTS

| | | | |
|---|---|---|---|
| 8,998,955 B2 | 4/2015 | Calvosa et al. | |
| 2005/0010298 A1* | 1/2005 | Zucherman | A61B 17/7068 606/279 |
| 2007/0016303 A1* | 1/2007 | Jackson | A61B 17/7062 623/17.16 |

(Continued)

FOREIGN PATENT DOCUMENTS

| | | |
|---|---|---|
| WO | 2006102269 A2 | 9/2006 |
| WO | 2012069877 A1 | 5/2012 |

(Continued)

OTHER PUBLICATIONS

Written Opinion mailed Jan. 22, 2021 to Diametros Medical S.R.L. for PCT/IB2020/053352 filed Apr. 8, 2020.

(Continued)

*Primary Examiner* — Julianna N Harvey
(74) *Attorney, Agent, or Firm* — Vorys, Sater, Seymour and Pease LLP

(57) ABSTRACT

An interspinous vertebral distractor (1) is provided, which is designed to be placed between two spinous processes and defining a longitudinal axis (1*a*), a sagittal plane (1*b*), and a frontal plane (1*c*), the distractor (1) comprises a base body (2) designed to be placed between the two spinous processes and defining a first end and a second end; an anchoring unit (3) designed to expand attaching the distractor (1) between two spinous processes; an actuator (5) designed to control the passage of the unit (3) between an expanded position and a contracted one; the base body (2) has a sagittal section with two opposing convexities so as to define a profile with two depressions (2*a*).

5 Claims, 7 Drawing Sheets

(56) References Cited

U.S. PATENT DOCUMENTS

| | | |
|---|---|---|
| 2007/0225807 A1 | 9/2007 | Phan et al. |
| 2008/0108990 A1 | 5/2008 | Mitchell et al. |
| 2008/0177306 A1* | 7/2008 | Lamborne .......... A61B 17/7062 623/17.11 |
| 2009/0234389 A1* | 9/2009 | Chuang .............. A61B 17/7065 606/249 |
| 2009/0254185 A1 | 10/2009 | Doellinger |
| 2009/0265006 A1* | 10/2009 | Seifert ................ A61B 17/025 623/17.11 |
| 2009/0306715 A1* | 12/2009 | Jackson ............. A61B 17/7062 606/279 |
| 2012/0078302 A1 | 3/2012 | Reimels |
| 2012/0123547 A1* | 5/2012 | Holzwarth ......... A61B 17/7062 623/17.16 |
| 2012/0330360 A1* | 12/2012 | Nishida ............. A61B 17/7062 606/249 |
| 2016/0206352 A1 | 7/2016 | Hess et al. |
| 2017/0348028 A1 | 12/2017 | Calvosa et al. |

FOREIGN PATENT DOCUMENTS

| | | |
|---|---|---|
| WO | 2021205209 A1 | 10/2021 |
| WO | 2021205210 A2 | 10/2021 |
| WO | 2021205211 A1 | 10/2021 |

OTHER PUBLICATIONS

Written Opinion and International Search Report mailed Jan. 12, 2021 to Diametros Medical S.R.L. for PCT/IB2020/053350 filed Apr. 8, 2020.

Written Opinion and International Search Report mailed Jan. 13, 2021 to Diametros Medical S.R.L. for PCT/IB2020/053353 filed Apr. 8, 2020.

* cited by examiner

INTERSPINOUS VERTEBRAL DISTRACTOR

This invention concerns an interspinous vertebral distractor/interspinous vertebral distraction device/interspinous vertebral distraction procedure of the type specified in the preamble of the first claim.

In particular, the invention relates to an implant designed to be implanted, preferably percutaneously, in an interspinous space to space two adjacent vertebrae apart.

As is well known, interspinous distraction can be surgically achieved by introducing an interspinous vertebral distractor between two spinous processes that is controlled by an operator-controlled device for inserting and controlling the distractor.

Distractors are prostheses designed to be implanted in the space between the spinous processes of two adjacent vertebrae, in order to maintain an intervertebral distraction that is suitable for limiting the loads transmitted between the vertebrae in case of intervertebral disc degenerative diseases, thus limiting associated pain.

They mainly consist of a base body that can be arranged between the spinous processes and the distractor's expansion anchoring means. The expansion of the anchoring means is controlled by the control device.

The interspinous vertebral distraction procedure consists in positioning a distractor in the space between the spinous processes of two adjacent vertebrae. In detail, with the patient in the prone position, the affected intervertebral space is identified, the spinous processes are brought closer through expansion cannulae, the measurement of the distractor to be inserted is determined by means of a probe and, finally, the selected distractor is inserted.

A first example of a procedure and distraction device and, in particular, a distractor is described in WO2006102269. In this case the distractor has a first ogive end so as to penetrate the intervertebral space, which is formed by a first pair of wings that open; the opposite end is equipped with a second pair of fixed wings enclosing the column between the two pairs of wings.

Another example is described in document U.S. Pat. No. 8,998,955 wherein there are two pairs of mobile wings. Each wing has one end hinged to the base body and the other end is free. To carry out the locking, this patent prescribes rotating the wings at angles greater than 120° so as to have the free ends facing the vertebrae.

An additional example is described in WO2012069877 where locking and the relative ease of introduction and extraction are achieved by means of hooked wings. The described prior art comprises some significant drawbacks.

In particular, despite the solutions outlined above, the interspinous vertebral distraction procedure/device, and, in particular, the distractor, are relatively complicated and, therefore, particularly expensive. This is mainly due to the fact that during the procedure, the operator encounters particular difficulties in inserting and defining a stable positioning of the interspinous vertebral distractors.

Another drawback is the low stability of the interspinous vertebral distractors once they have been implanted.

An equally important drawback is the fact that the control kinematics of the mobile wings is particularly complex.

Another drawback is, thus, the costs and difficulties in implementing the known interspinous vertebral distractors.

In this context, the technical task underlying this invention is to devise an interspinous vertebral distractor/interspinous vertebral distraction device/interspinous vertebral distraction procedure able to substantially overcome at least some of the drawbacks mentioned above.

Said technical task comprises the important purpose of the invention's having an interspinous vertebral distractor that, once implanted, is easy to insert and stable.

Another objective is to provide an interspinous vertebral distractor that is easy to implement and, therefore, costs less.

The technical task and the specified purposes are achieved by an interspinous vertebral distractor/interspinous vertebral distraction device/interspinous vertebral distraction procedure as claimed in Claim 1. Examples of preferred embodiments are described in the dependent claims.

The characteristics and advantages of the invention are clarified by the following detailed description of preferred embodiments thereof, with reference to the accompanying drawings, wherein.

In this document, the measures, values, shapes, and geometric references (such as perpendicularity and parallelism), when used with words like "about" or other similar terms such as "approximately" or "substantially", are to be understood as except for measurement errors or inaccuracies due to production and/or manufacturing errors and, above all, except for a slight divergence from the value, measure, shape, or geometric reference which it is associated with. For example, if associated with a value, such terms preferably indicate a divergence of no more than 10% of the value itself.

Furthermore, when used, terms, such as "first", "second", "higher", "lower", "main", and "secondary" do not necessarily identify an order, relationship priority, or relative position, but they can simply be used to distinguish different components more clearly from one another.

The measurements and data provided in this text are to be considered as performed in ICAO International Standard Atmosphere (ISO 2533), unless otherwise indicated. With reference to the figures, the reference number 1 indicates, as a whole, the interspinous vertebral distractor according to the invention.

The distractor 1 is a percutaneous device that can be implanted for interspinous distraction. It is designed to be implanted in an interspinous space so that it is interposed between two adjacent vertebrae and, thus, spaces two spinous processes apart.

The distractor 1 defines a longitudinal axis 1a that is, suitably, barycentric.

Figure 1:
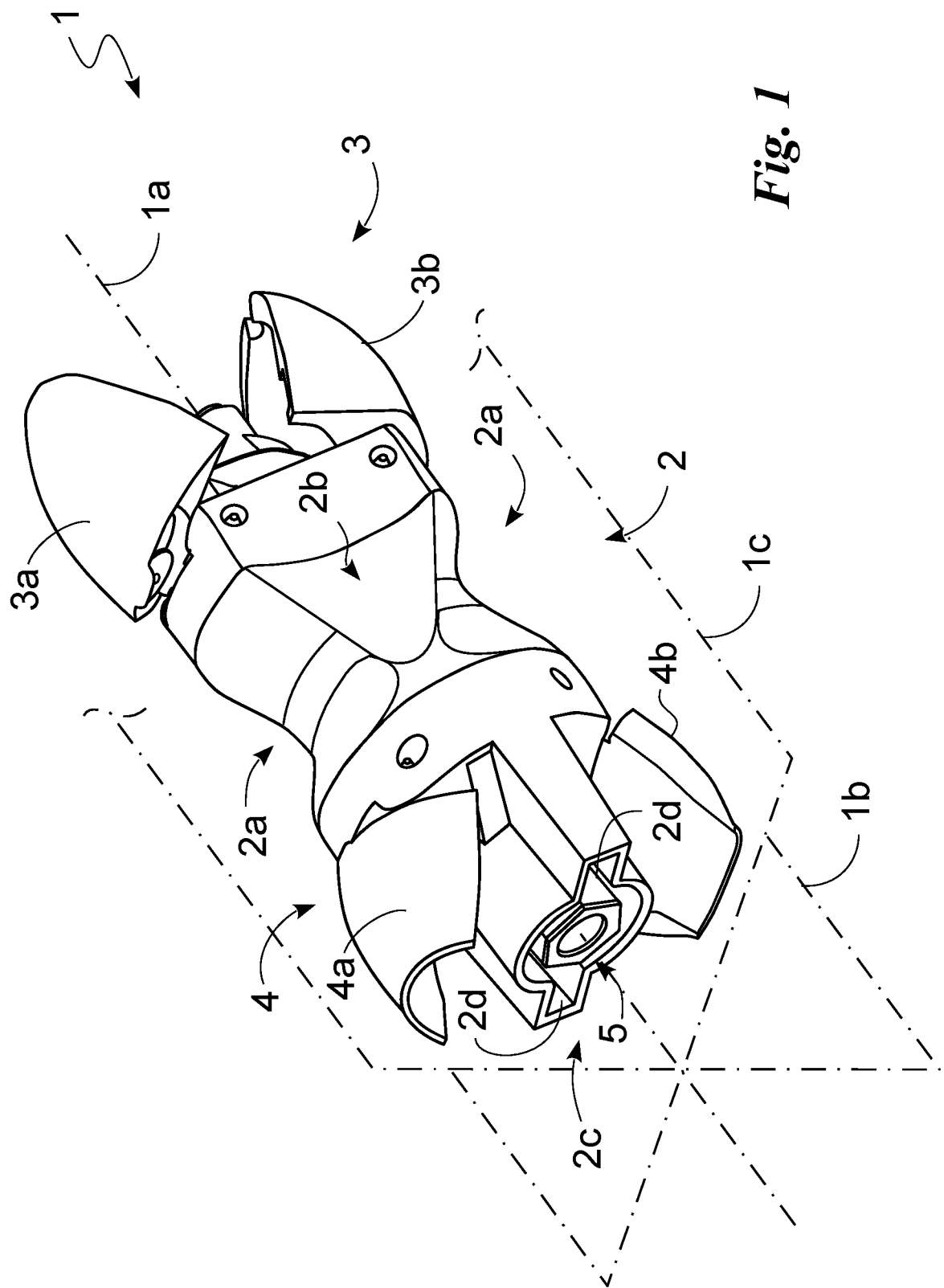
FIG. 1 shows, to scale, an interspinous vertebral distractor according to the invention.

It defines a sagittal plane 1b that is, suitably, barycentric; and/or a frontal plane 1c that is, suitably, barycentric (FIG. 1).

The sagittal plane 1b is perpendicular to the frontal plane 1c.

The intersection between the sagittal plane 1b and the frontal plane 1c defines the axis 1a.

The distractor 1 preferably comprises a base body 2 that is designed to be placed between two spinous processes by spacing them apart.

The base body 2 defines, in relation to the longitudinal axis 1*a*, a first end and a second end.

The base body 2 preferably has a sagittal section (i.e. defined by the intersection of the sagittal plane 1*b* with the base body 2) with at least one convexity defining a depression 2*a* housing a spinous process.

Figure 3:
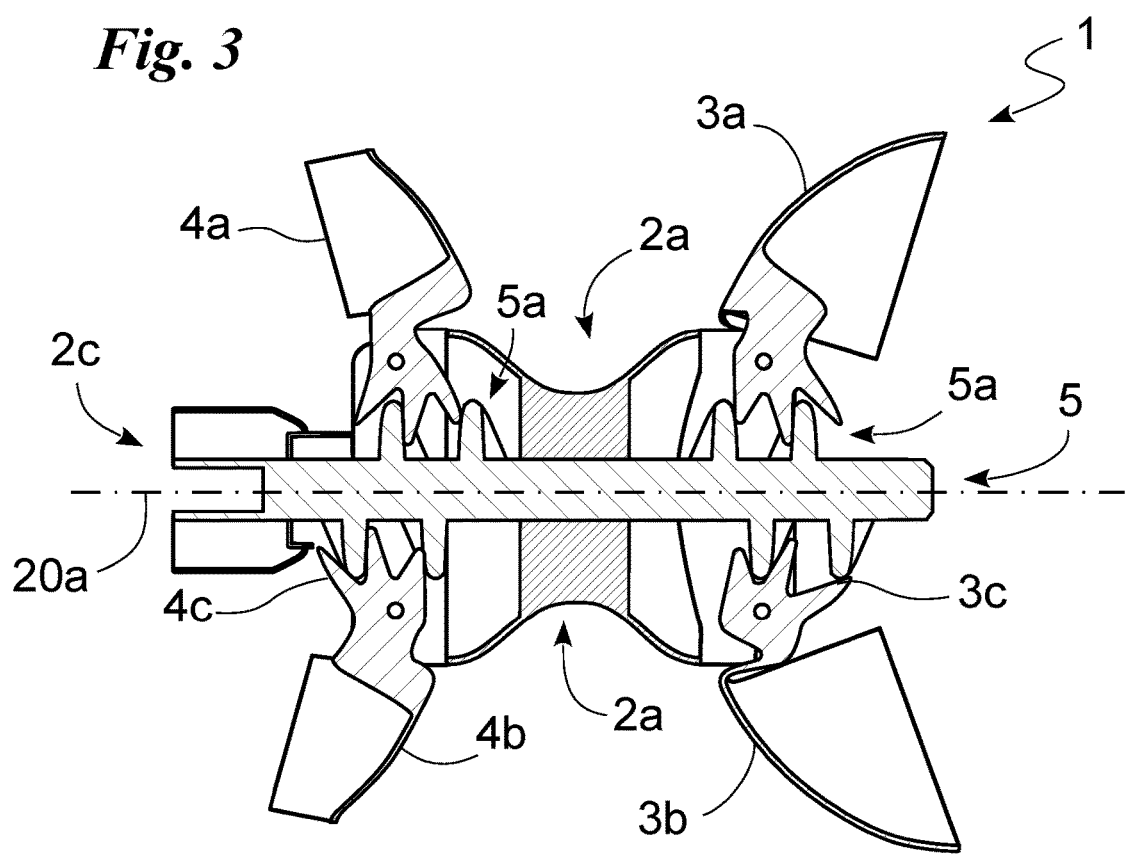
FIG. 3 shows, to scale, a cross-section of the distractor in FIG. 1.

In detail, and as illustrated in FIG. 3, said sagittal section has two convexities and, therefore, two depressions 2*a* placed opposite the frontal plane 1*c* and each one is designed to accommodate a spinous process. The depressions 2*a* preferably is specular to the frontal plane 1*c* and, therefore, the sagittal section is symmetrical in relation to the frontal plane 1*c*.

The base body 2 preferably has the minimum sagittal height at the bottom of the at least one depression 2*a* and, preferably, the maximum sagittal height at the apex of the at least one depression 2*a*.

In this document, the expression "sagittal height" identifies a length calculated perpendicular to the frontal plane 1*c*.

The minimum sagittal height of the base body 2 preferably is basically less than 100%, in detail less than 85%, and in more detail less than 65% of the maximum sagittal height of the same base body 2.

The profile of the depression 2*a* preferably is elliptical with a suitable eccentricity of less than 1, in detail less than 0.95, and in more detail basically ranging between 0.95 and 0.75, and preferably between 0.9 and 0.8.

The base body 2 preferably has a frontal section (i.e. defined by the intersection of the frontal plane 1*c* with the base body 2) tapered with a minimum section close to the first end. In detail, the frontal section preferably comprises a first proximal sector at the first end of a minimum and suitably constant frontal height; a second proximal sector at the second end of a maximum and suitably constant frontal height; and a central sector joining the first and second sectors and, thus, defining at least one slope 2*b* between the first and second sectors.

In this document, the expression "frontal height" identifies a length calculated perpendicular to the sagittal plane 1*b*.

The central sector preferably has an increasing monotonic frontal height.

The at least one slope 2*b* is formed at the depressions 2*a*.

The radial section of the base body 2 made at the bottom of the depressions 2*a* has a frontal height and sagittal height basically equal to each other. Said radial section can preferably be circle-shaped.

The start of the slope 2*b*, i.e. the central sector, is at a shorter axial distance from the first end than the bottom of the depressions 2*a*.

In this document, the terms "radial" and "axial" identify a direction/plane respectively perpendicular and parallel to the longitudinal axis 1*a*.

The maximum frontal height and maximum sagittal height preferably is almost equal.

The minimum frontal height preferably is less than the minimum sagittal height.

The central sector has two slopes 2*b* on opposite sides to the sagittal plane 1*b* and suitably almost specular to each other in relation to the sagittal plane 1*b*. Consequently, the central sector and, thus, the base body 2 preferably is specular to the sagittal plane 1*b*.

The base body 2 preferably is hollow.

The distractor 1 preferably comprises a unit 3 for locking the distractor 1 at the spinous processes and, to be precise, between the spinous processes.

The unit 3 is attached to the base body 2 at the first end and can be moved in relation to the body 2 so as to expand radially (in particular perpendicularly to the frontal plane 1*c*) locking the distractor 1 between the spinous processes.

The unit 3 is designed to define at least one expanded position wherein it has a maximum radial expansion; and at least one contracted position wherein it has a minimum radial expansion.

The unit 3 defines the head of the distractor 1 entering between the spinous processes.

The unit 3 preferably comprises at least one wing hinged to the base body 2 at the first end defining the rotation axis, which is, suitably, almost parallel to the frontal plane 1*c*. In detail, it comprises a first wing 3*a* hinged to the base body 2 and a second wing 3*b* hinged to the base body 2 on the opposite side to the first wing 3*a* in relation to the frontal plane 1*c*.

The wings 3*a* and 3*b* preferably has rotation axes that are basically parallel to each other.

The wings 3*a* and 3*b* preferably rotates simultaneously and in the opposite direction during a change in the position of the unit 3.

They preferably have a tapered axial profile with a minimum section distal to the base body 2 so that, in the contracted position, the locking unit 3 is axially tapered and, in particular, ogive.

The wings 3*a* and 3*b* preferably has a U-shaped radial section with an opening facing the longitudinal axis 1*a*.

The distractor 1 preferably comprises an additional unit 4 for locking the distractor 1 at the spinous processes and, to be precise, between the spinous processes.

The additional unit 4 is attached to the base body 2 at the second end and can be moved in relation to the body 2 so as to expand radially (in particular perpendicularly to the frontal plane 1*c*) locking the distractor 1 between the spinous processes.

The additional unit 4 is designed to define an additional expanded position wherein it has maximum radial expansion; and an additional contracted position wherein it has minimum radial expansion.

The additional unit 4 preferably comprises at least one additional wing hinged to the base body 2 at the second end with the rotation axis suitably almost parallel to the frontal plane 1*c*. In detail, it comprises a first additional wing 4*a* hinged to the base body 2 and a second additional wing 4*b* hinged to the base body 2 on the opposite side to the first additional wing 4*a* in relation to the frontal plane 1*c*.

The additional wings 4*a* and 4*b* have rotation axes basically parallel to each other and, in detail, to the wings 3*a* and 3*b*.

The additional wings 4*a* and 4*b* rotate simultaneously and in the opposite direction during a change in the position of the additional unit 4.

The distractor 1 preferably comprises an actuator 5 designed to control the passage of the distractor 1 between an anchoring configuration and an un-anchoring configuration.

In the anchoring configuration, the unit 3 is in the expanded position locking the distractor 1 in the correct position; and, suitably, the additional unit 4 is in the additional expanded position locking the distractor 1 on the opposite side of the unit 3 in relation to the depression 2*a*.

In the un-anchoring configuration, the unit 3 is in the contracted position and not locking the distractor 1 in the correct position; and, suitably, the additional unit 4 is in the additional contracted position.

The actuator 5 is designed to rotate, specifically exclusively, about the longitudinal axis 1*a* in relation to the base body 2 by controlling a change in the configuration of the distractor 1.

Figure 5:
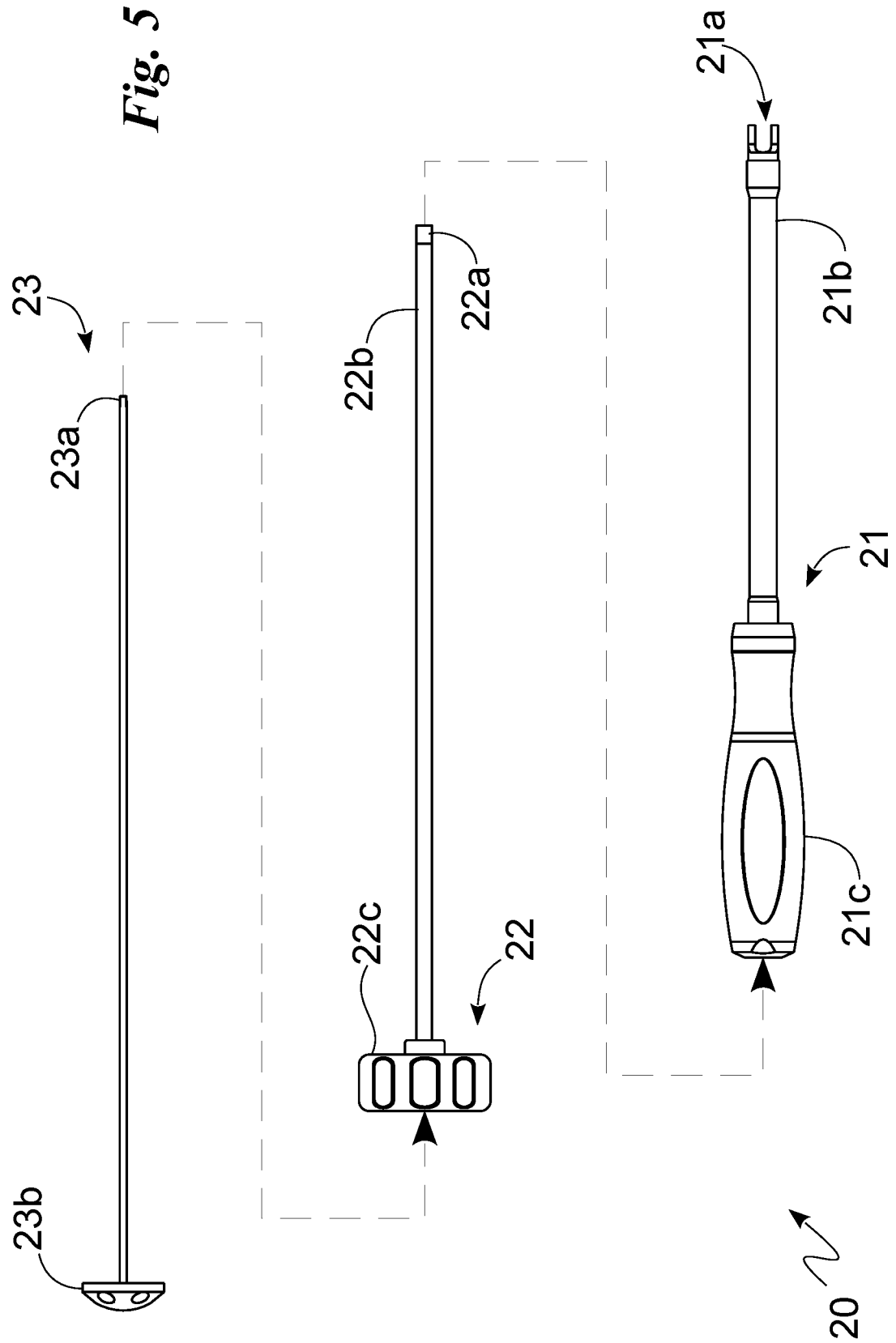
FIG. 5 illustrates, to scale, the assembly in FIG. 4.

The actuator 5, shown in FIG. 5, preferably comprises a control thread 5*a* of the unit 3 and, suitably, an additional control thread 5*b* of the additional unit 4.

The additional thread 5*b* preferably is opposite the thread 5*a*.

To this end, the unit 3 preferably comprises, for each wing 3*a* and/or 3*b*, at least one thread 5*a* engagement tooth 3*c* that, when pushed by the actuator 5, controls the rotation of the wings 3*a* and/or 3*b*.

The additional unit 4 preferably comprises, for each additional wing 5*a* and/or 5*b*, at least one additional thread 5*b* engagement tooth 4*c* that, when pushed by the actuator 5, controls the rotation of the additional tooth 4*c* by controlling the rotation of the additional wings 4*a* and/or 4*b*.

The actuator 5 is externally controlled and the base body 2 comprises an opening 2*c* for accessing the actuator 5 at the second end.

The opening 2*c* is always in view, i.e. accessible from the outside, regardless of the configuration of the distractor 1. The additional unit 4 in the contracted position is, therefore, folded over the base body 2 leaving the opening 2*c* in view.

The actuator 5 is at least partially housed in the base body 2.

The distractor 1 can be part of an interspinous vertebral distraction device 10.

The distraction device 10 comprises the distractor 1, previously described, and a control 20 for the distractor 1.

Figure 4:
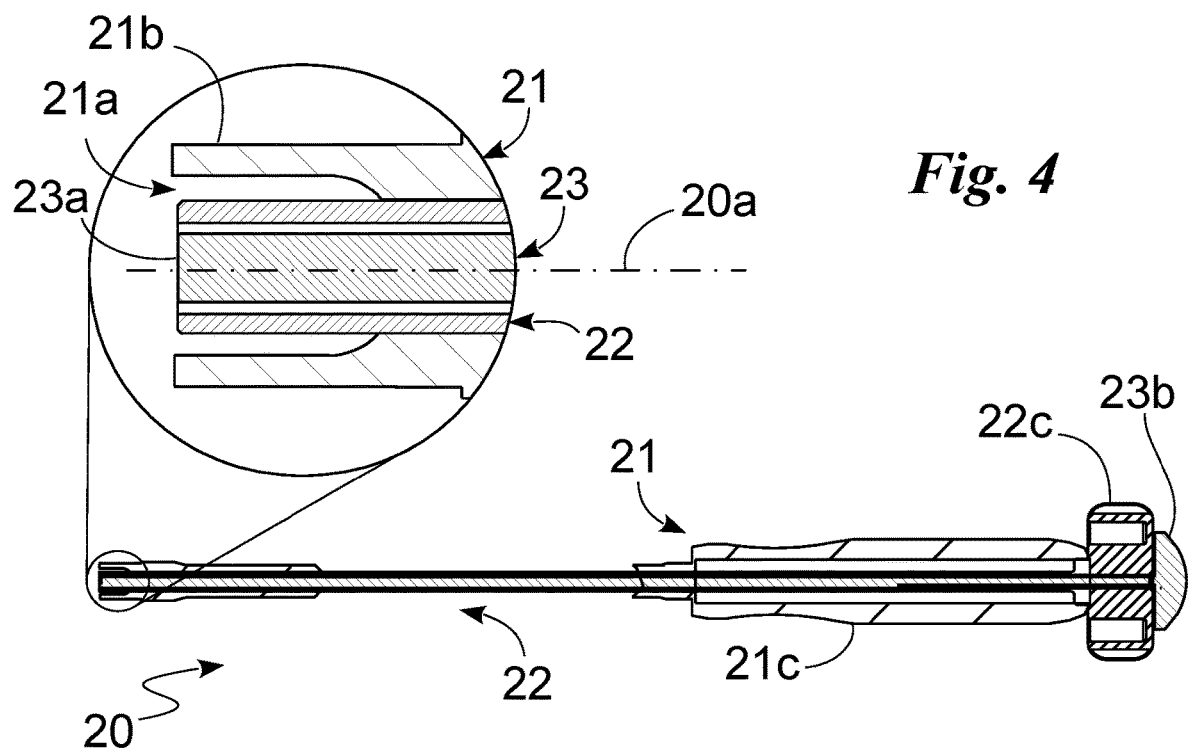
FIG. 4 shows, to scale, an assembly of an interspinous vertebral distraction device according to the invention.

The control 20, as presented in FIGS. 4 and 5, defines a main extension axis 20*a* that is preferably barycentric.

It is designed to be engaged with the distractor 1 at the opening 2*c* suitably arranging the axes 1*a* and 20*a* basically parallel to each other and, more specifically, so that they basically coincide.

The control 20 preferably comprises a first tool 21 for controlling the rotation of the distractor 1.

The first tool 21 is designed to define a first rotational constraint with, suitably exclusively, the base body 2 i.e. a constraint that prevents their mutual rotation about the axes 1*a* and/or 20*a*.

It comprises first means 21*a* designed to be engaged with the body 2, suitably at the opening 2*c*, defining said first rotational constraint.

The first means 21*a* preferably comprises at least one tip and the base body 2 preferably comprises at least one seat 2*d* for inserting said tip. In particular, they comprise two tips located on opposite sides of the axis 1*a* and the base body 2 comprises a seat 2*d* for each tip.

The first tool 21 comprises a hollow channel 21*b* and, thus, defines a channel designed to be placed in communication with the opening 2*c* when the first tool 21 is attached to the base body 2.

The channel 21*a* is parallel to the main extension axis 20*a*.

The first means 21*b* protrude from the channel 21*b* along the main extension axis 20*a*.

The first tool 21 preferably comprises a grip 21*c* connected to the channel 21*b* on the opposite side to the means 21*a*.

The control 20 preferably comprises a second tool 22 for controlling the change in configuration of the distractor 1.

The second tool 22 is designed to define a second rotational constraint with, suitably exclusively, the actuator 5 i.e. a constraint that prevents their mutual rotation about the axes 1*a* and/or 20*a*.

It comprises second means 22*a* designed to be engaged with the actuator 5, suitably at the opening 2*c*, defining said second rotational constraint The second constraint is basically an interlocking mechanism. For example, the actuator 5 preferably comprises a polygonal (e.g. hexagonal) end that is in view of the opening 2*c* and the second means 22*a* preferably defines a counter-shaped engagement seat at said end.

The second tool 22 preferably rotates in relation to the base body 2 and the first tool 21 about the extension axis 20*a*.

It can be inserted into the channel 21*a*.

The second tool 22 preferably comprises an additional hollow channel 22*b* and define an additional channel designed to be placed in communication with the opening 2*c* when the second tool 22 is attached to the actuator 5.

The additional channel 22*a* is parallel to the main extension axis 20*a*.

The second tool 22 preferably comprises a head 22*c* for controlling the second tool 22.

The head 22*c* is designed to be placed outside the first tool 21 when the second tool 22 is in the channel 21*b*.

The control 20 preferably comprises a third tool 23 axially constraining at least one of the tools 21 and 22 to the distractor 1.

The third tool 23 is designed to be engaged with the actuator 5 by defining said axial constraint and, thus, preventing axial motion of the first tool 21 and/or of the second tool 22 in relation to the distractor 1.

It preferably comprises third means 23*a* defining said axial constraint.

The third tool 23 preferably comprises a gripping element 23*b* for controlling the third tool 23.

The gripping element 23*b* is designed to be placed outside the first tool 21 and the second tool 22 when the third tool 23 is in the additional channel 22*b*.

The third means 23*a* preferably defines a threaded coupling with the actuator 5.

The third tool 23 can be at least partially arranged in the additional channel.

Figure 7:
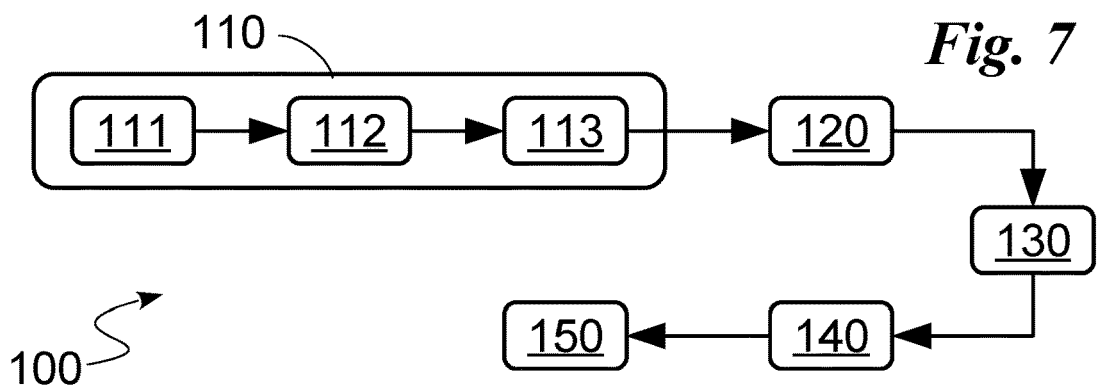
FIG. 7 schematises the interspinous vertebral distraction procedure according to the invention.

The operation of the distractor 1 and of the distraction device 10, described above in structural terms, define an innovative interspinous vertebral distraction procedure 100 that is schematised in FIG. 7.

The procedure 100 comprises the distractor 1 and, in particular, the distraction device 10.

The procedure 100 preferably comprises a preparation step 110 in which the control 20 is attached to the distractor 1.

Figure 6A:
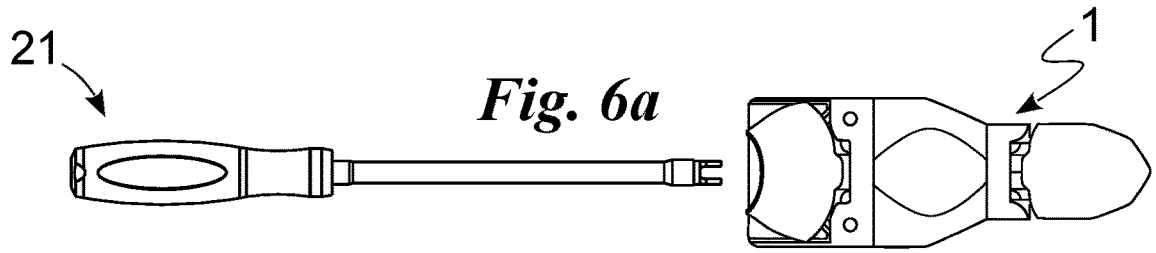
FIGS. 6a-6f represent, to scale, a preparation sequence for the interspinous vertebral distraction device according to the invention.
Figure 6B:
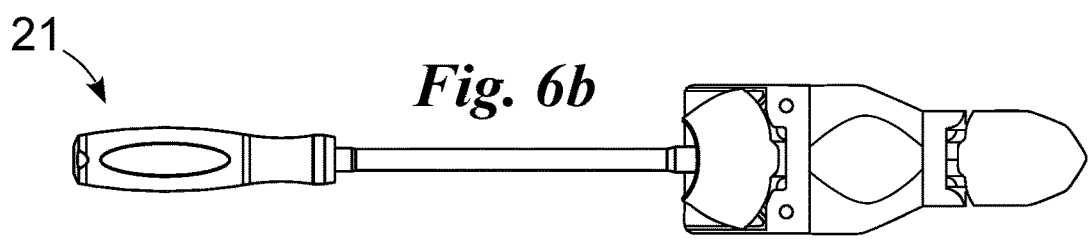

The preparation step 110 preferably comprises a first constraint sub-step 111 (FIGS. 6*a*-6*b*) wherein the first tool 21 is engaged to the base body 2 defining said first rotational constraint. In detail, the first constraint is implemented thanks to the first means 21*a* by inserting the at least one tip in the at least one seat 2*b*.

Figure 6C:
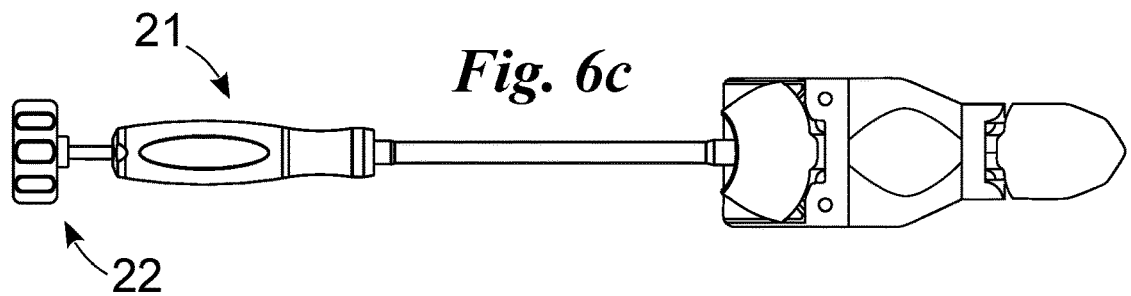
Figure 6D:
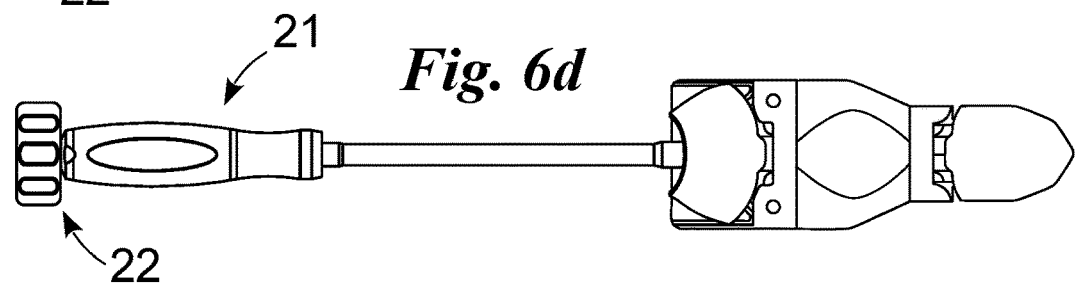

The preparation step 110 preferably comprises a second constraint sub-step 112 (FIGS. 6*c*-6*d*) wherein the second tool 22 is engaged with the actuator 5 defining said second rotational constraint. In detail, the first constraint is implemented by coupling the second means 22a to the actuator 5 by interference.

In the sub-step 112, the second tool 22 is inserted into the channel 21b.

Figure 6E:
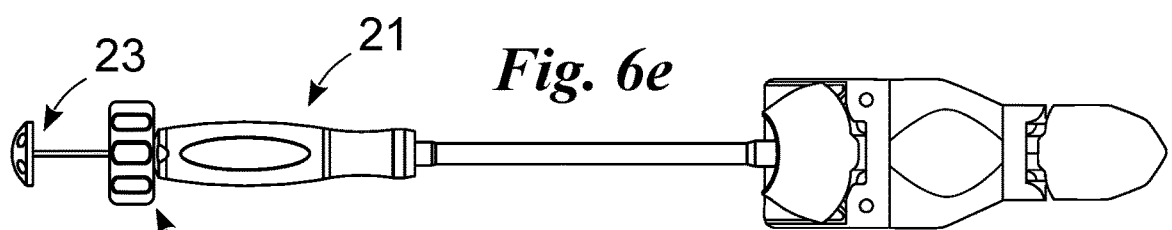
Figure 6F:
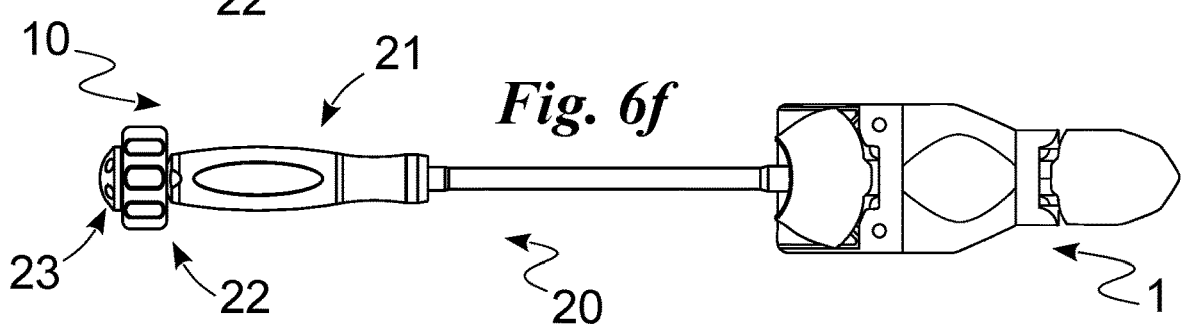

The preparation step 110 preferably comprises a third constraint sub-step 113 (FIGS. 6d-6e) wherein the third tool 23 is designed to be engaged to the actuator 5 defining said axial constraint.

At the end of the preparation step 110, the distractor 1 is in the un-anchoring configuration.

Figure 2A:
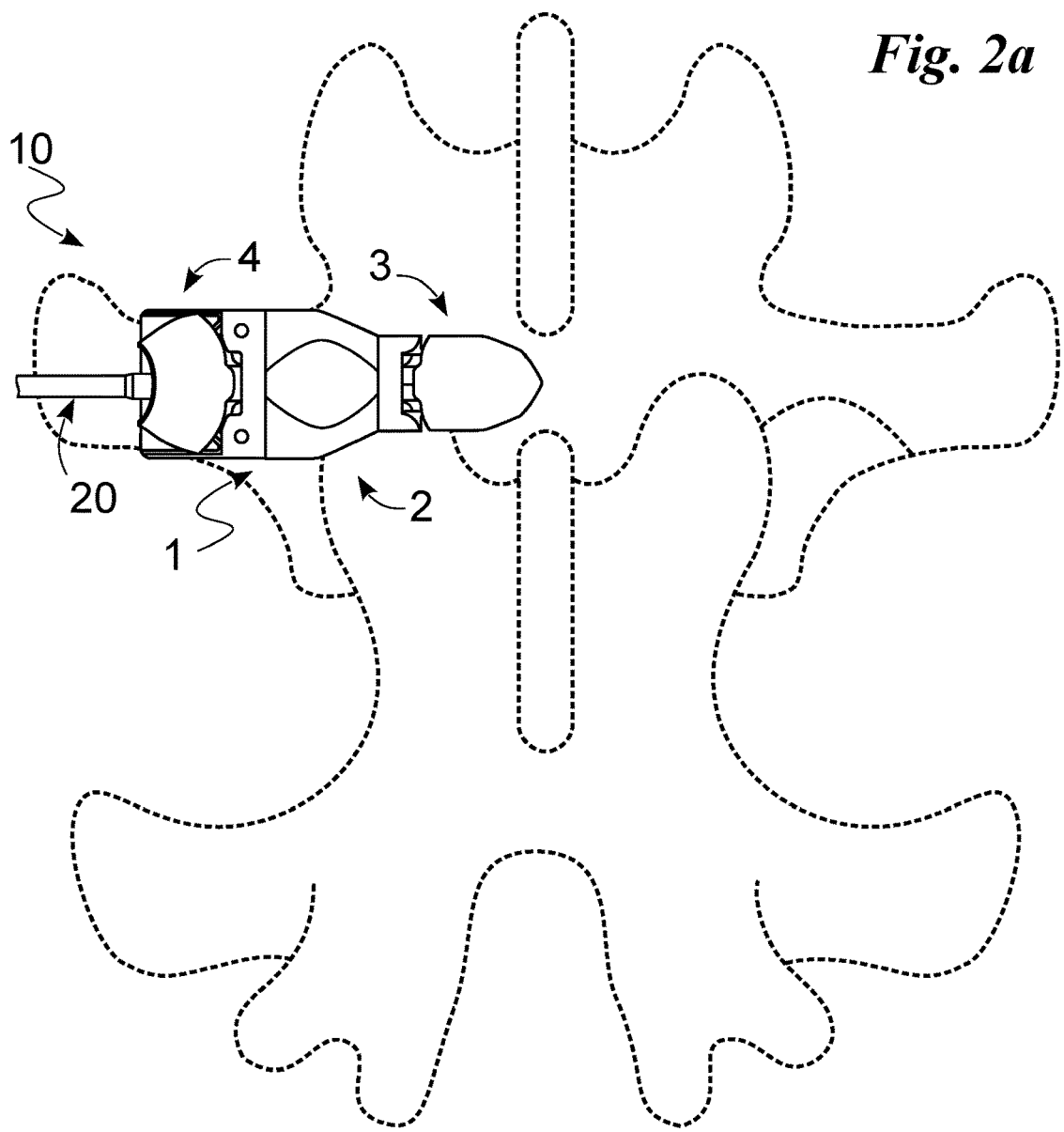
FIGS. 2a-2e illustrate, to scale, the distractor in a sequence during an interspinous vertebral distraction procedure according to the invention.
Figure 2B:
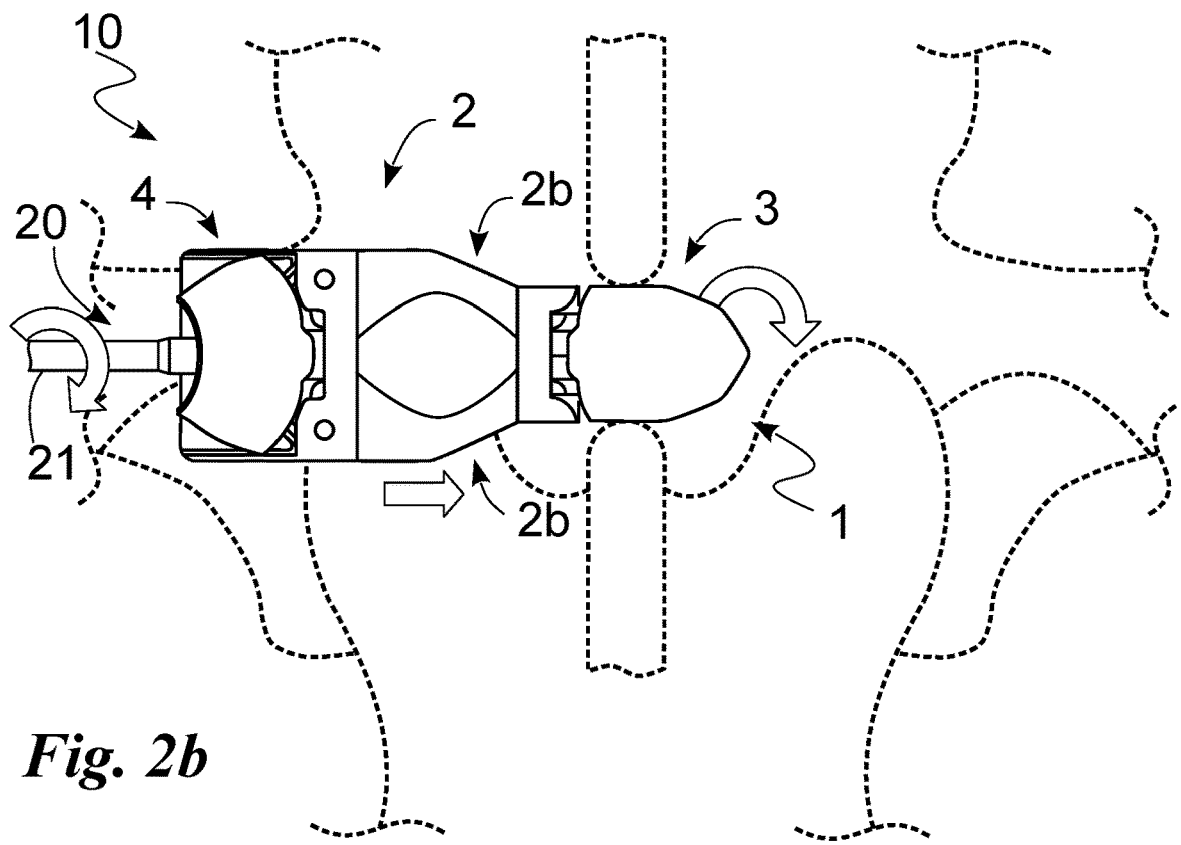

The procedure 100 preferably comprises a positioning step 120 (FIGS. 2a-2b) wherein the distractor 1, suitably controlled by the control 20 and, in particular, by the first tool 21, is brought near the spinous processes.

In this step 120, the distractor 1 is placed with the frontal plane 1c basically perpendicular to the patient's frontal plane and then moved along the longitudinal axis 1a bringing the locking unit 3 basically to the two spinous processes. The distractor 1 then moves axially forward so that the unit 3, in the contracted position, penetrates between the spinous processes and, thanks to its tapered profile, is arranged between them.

The step 120 ends when the at least one slope 2b is proximal to the spinous processes.

Figure 2C:
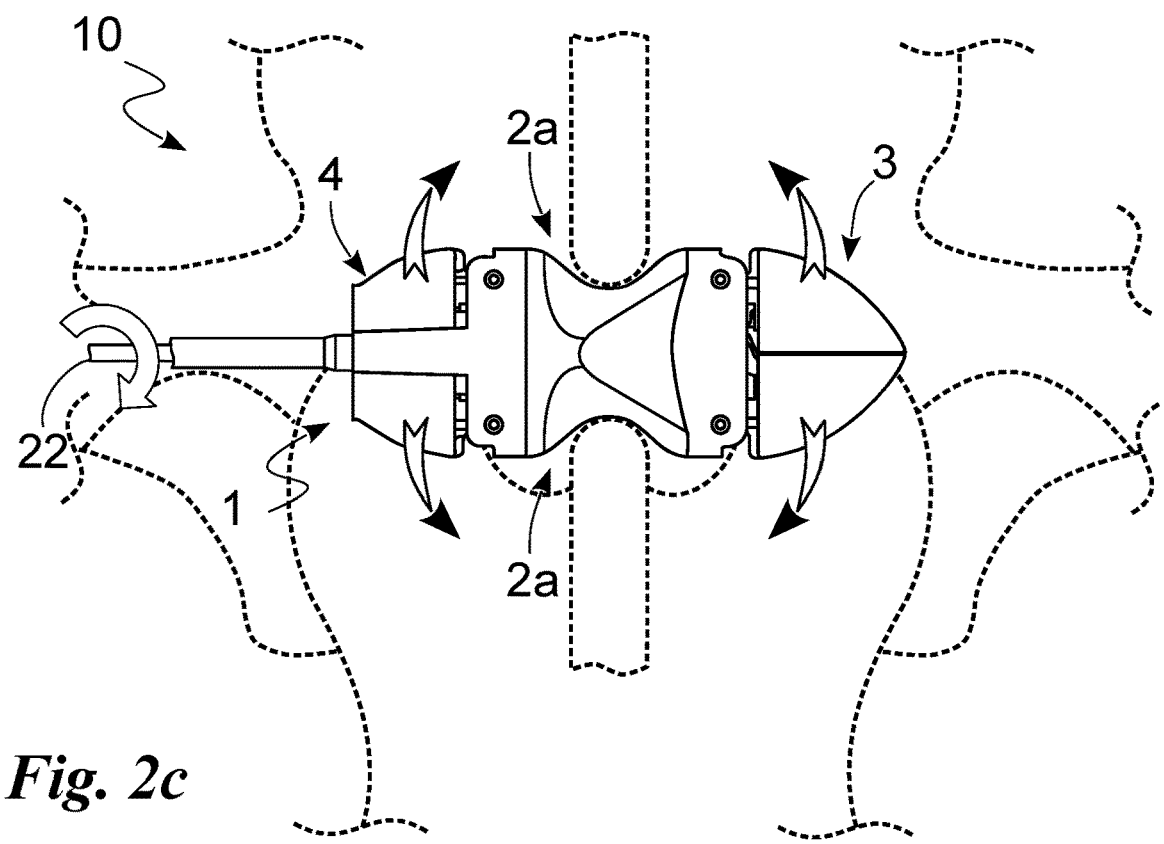

The procedure 100 preferably comprises an insertion step 130 (FIGS. 2b-2c) wherein the base body 2 and, in detail, the entire distractor 1 rotate about the longitudinal axis 1a arranging the frontal plane 1c basically parallel to the patient's frontal plane and, thus, the two spinous processes in the depressions 2a.

In this step 130, the first tool 21 rotates the distractor 1 and, to be precise, axially moves the distractor 1 and, preferably simultaneously, rotates it about the longitudinal axis 1a.

The axial translation causes the spinous processes to slide along the slopes 2b so that they gradually adapt to the profile of the sagittal section and, thus, to the at least one depression 2a.

The rotation enables the depressions 2a to appear and, thus, to house the spinous processes inside, suitably after they have travelled at least part of the slopes 2b. During the insertion step 130, the distractor 1 is rotated by an angle basically ranging between 60° and 120°, in detail between 75° and 105°, and preferably around 90°.

Figure 2D:
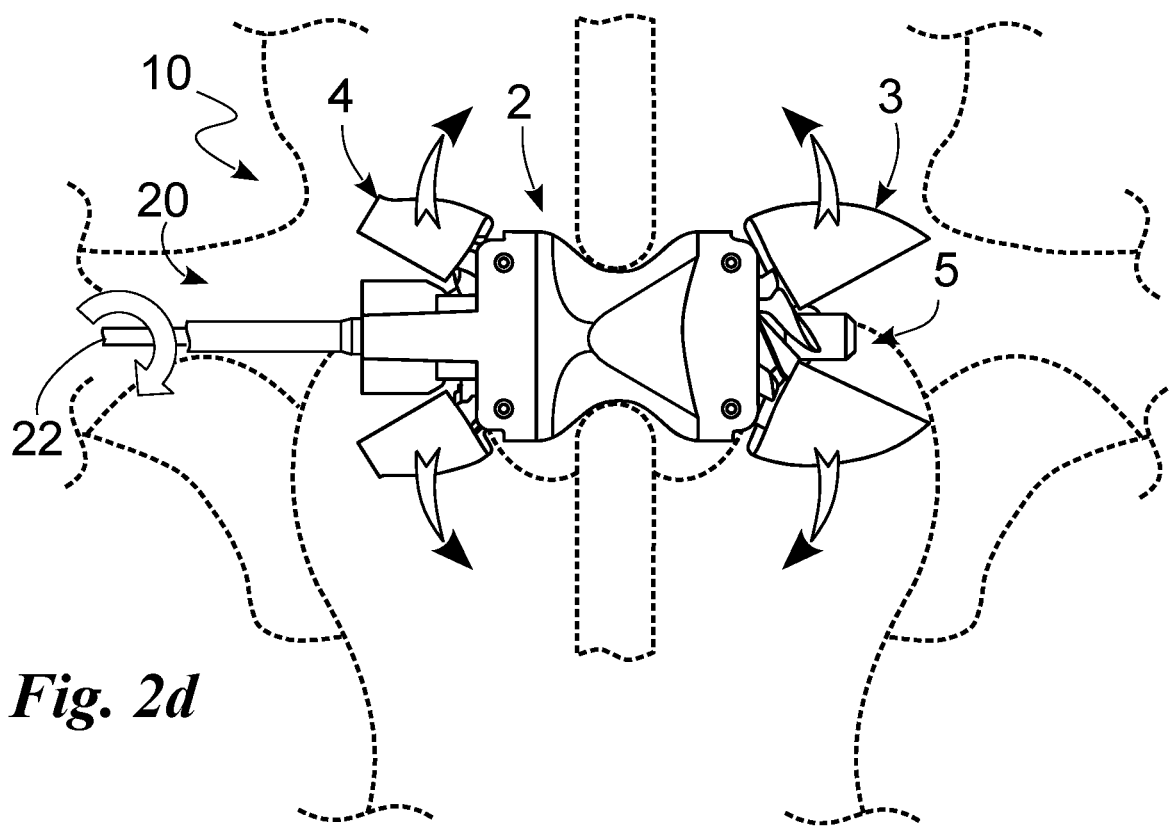

The procedure 100 preferably comprises an expansion step 140 (FIGS. 2c-2d) wherein the distractor 1 switches from the anchoring configuration to the un-anchoring configuration.

In the expansion step 140, the actuator 5, controlled by the second tool 22, causes the unit 3 to pass into the expanded position so as to constrain the distractor 1 between the spinous processes.

At the same time, the actuator 5 suitably controls the passage of the additional unit 4 into the additional expanded position so as to constrain the distractor 1 between the spinous processes on the opposite side to the unit 3 in relation to the depressions 2a.

It should be noted that the variation in the configuration of the distractor 1 is controlled by rotating the second tool 22 in relation to the first tool 21 that, suitably, remains substantially still.

Figure 2E:
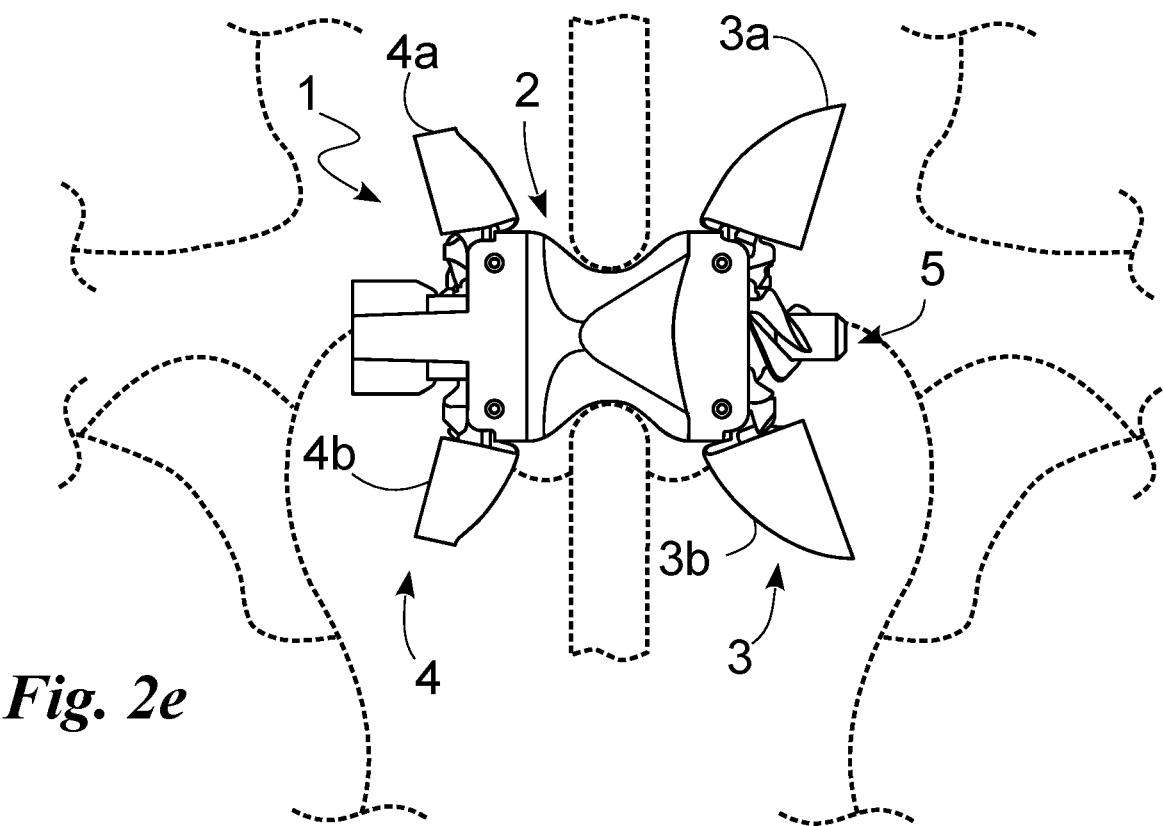

The procedure 100 preferably comprises a removal step 150 (FIG. 2e) for moving the control 20 away from the distractor 1.

In this step 150, the third tool 23 is disengaged from the actuator 5; then the second tool 23 and then the first tool 21 are moved away from the distractor 1.

The distractor 1, the vertebral distraction device 10 and, thus, the interspinous vertebral distraction procedure 100 according to the invention achieve important advantages.

In fact, thanks to the particular conformation of the distractor 1 and/or the practicality of the distractor control defined by control 20, they are particularly simple and quick to use and, in particular, enable a precise, firm, and rapid positioning of the distractor 1 between the spinous processes.

An important advantage is, therefore, the high stability of the distractor 1 once implanted. In fact, thanks to the depressions 2a, for example, the distractor 1 has a precise housing for each spinous process.

These advantages are enhanced by the presence of slopes 2b that, by gradually spacing the spinous processes apart, make it possible to carry out both a rapid and precise positioning of the distractor 1 and a less invasive procedure for the patient. Another important advantage is the particular control 20 that makes it possible to have a precise and practical control of the distractor 1 and, in particular, of the wings 3a and 3b and, suitably, of the additional wings 4a and 4b.

A significant advantage is that the distractor 1 (and, thus, the vertebral distraction device 10 and procedure 100) have low costs.

Variations preferably is made to the invention that fall within the scope of the inventive concept defined in the claims. All details preferably are replaced with equivalent elements and the scope of the invention includes all other materials, shapes, and dimensions.

The invention claimed is:

1. An interspinous vertebral distractor designed to be placed between two spinous processes and defining a longitudinal axis, a sagittal plane, and a frontal plane; said distractor comprising:
   a base body designed to be placed between said two spinous processes and defining, in relation to said longitudinal axis, a first end and a second end;
   an anchoring unit firmly attached to said base body at said first end and designed to expand perpendicularly to said frontal plane;
   an actuator designed to control the passage of said unit between an expanded position wherein said unit constrains said distractor between said two spinous processes and a contracted position wherein said unit does not constrain said distractor between said two spinous processes;
   wherein said base body has a sagittal section with two opposing convexities so as to define a profile with two depressions placed on the opposite side of said frontal plane each of which is designed to accommodate one of said two spinous processes;
   wherein said base body has a tapered frontal section with a minimum section at the first end;
   wherein the frontal section of said base body comprises a first sector, a second sector, and a central sector;
   wherein said first sector is at said first end and has a minimum height, wherein said second sector is at said second end and has a maximum height;
   wherein said central sector defines two slopes joining said first sector and said second sector placed on the opposite side to said sagittal plane.

2. The distractor according to claim 1, wherein said depressions are formed on at least one slope.

3. The distractor according to claim 2, wherein the beginning of said slope has a shorter axial distance from said first end than the bottom of said depressions.

4. The distractor according to claim 2, wherein a radial section of said base body made at said bottom of said depressions has a frontal height and sagittal height equal to each other.

5. The distractor according to claim 1, wherein a sagittal height of said base body at the bottoms of said depressions is less than 85% of the sagittal height of said base body at the apexes of said depressions.

* * * * *